United States Patent
Farazi

(10) Patent No.: US 8,934,963 B1
(45) Date of Patent: Jan. 13, 2015

(54) METHOD AND APPARATUS FOR MONITORING ARRYTHMOGENIC EFFECTS OF MEDICATIONS USING AN IMPLANTABLE DEVICE

(75) Inventor: Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1805 days.

(21) Appl. No.: 11/623,613

(22) Filed: Jan. 16, 2007

(51) Int. Cl.
*A61B 5/0452* (2006.01)
*A61B 5/00* (2006.01)

(52) U.S. Cl.
CPC ........... *A61B 5/0452* (2013.01); *A61B 5/04525* (2013.01); *A61B 5/4848* (2013.01); *A61B 5/4839* (2013.01)
USPC ............................ 600/516; 600/515; 600/517

(58) Field of Classification Search
CPC .. A61B 5/4848; A61B 5/4839; A61B 5/0452; A61B 5/04525
USPC ......................................... 600/510, 515–517
See application file for complete search history.

(56) References Cited

U.S. PATENT DOCUMENTS

| | | | |
|---|---|---|---|
| 4,686,988 A | 8/1987 | Sholder | |
| 4,708,142 A | 11/1987 | DeCote, Jr. | |
| 4,729,376 A | 3/1988 | DeCote, Jr. | |
| 4,731,051 A | 3/1988 | Fischell | |
| 4,809,697 A | 3/1989 | Causey, III et al. | |
| 4,944,299 A | 7/1990 | Silvian | |
| 4,947,845 A | 8/1990 | Davis | |
| 4,969,467 A | 11/1990 | Callaghan et al. | |
| 5,350,410 A | 9/1994 | Kleks et al. | |
| 5,437,285 A * | 8/1995 | Verrier et al. ................. | 600/515 |
| 6,275,734 B1 | 8/2001 | McClure et al. | |
| 7,029,443 B2 | 4/2006 | Kroll | |
| 7,142,911 B2 | 11/2006 | Boileau et al. | |
| 2004/0267321 A1 * | 12/2004 | Boileau et al. .................... | 607/3 |
| 2008/0082016 A1 * | 4/2008 | Kohls et al. ................... | 600/516 |

OTHER PUBLICATIONS

F. Akar and D. Rosenbaum, Transmural Electrophysiological Heterogeneities Underlying Arrhythmogenesis in Heart Failure, Circ. Res. 93:638-645 (2003).
C. Antzelevitch, Cardiac repolarization. The long and short of it, Europace 7(s2): S3-S9 (2005).
Corlan et al., New quantitative methods of ventricular repolarization analysis in patients with left ventricular hypertrophy, Ital Heart J 1 (8): 542-548) (2000).
Engel et al., Electrocardiographic Arrhythmia Risk Testing, Curr Probl Cardiol 29:357-432 (2004).
Vincent, Ventricular Arrhythmias, Cardiology Clinics 18:2 (2000).
Yamaguchi et al., T wave peak-to-end interval and QT dispersion in acquired long QT syndrome: a new index for arrythmogenicity, Circulation 110:904 (2004).

* cited by examiner

*Primary Examiner* — Tammie K Heller

(57) ABSTRACT

An implantable device and method for monitoring changes in the risk of arrhythmia induced by medications. The implantable device monitors risk of arrhythmia by analyzing an aspect of T-wave morphology to generate a metric of transmural dispersion of repolarization ("TDR") as a proxy for the risk of arrhythmia. The implantable device generates an index of change in the risk of arrhythmia by comparing values of the metric of TDR obtained for different time periods. The implantable device generates a warning if the change in risk of arrhythmia is outside acceptable limits. The implantable device can also communicate with other devices to correlate changes in risk of arrhythmia with medications taken by the patient.

17 Claims, 7 Drawing Sheets

METHOD AND APPARATUS FOR MONITORING ARRYTHMOGENIC EFFECTS OF MEDICATIONS USING AN IMPLANTABLE DEVICE

BACKGROUND OF THE INVENTION

An arrhythmia is an abnormal heart rhythm. One example of an arrhythmia is bradycardia wherein the heart beats at an abnormally slow rate or wherein significant pauses occur between consecutive beats. Other examples of arrhythmias include tachyarrhythmias wherein the heart beats at an abnormally fast rate. With atrial tachycardia, the atria of the heart beat abnormally fast. With ventricular tachycardia, the ventricles of the heart beat abnormally fast. Though often unpleasant for the patient, atrial tachycardia is typically not fatal. However, some tachycardia, particularly ventricular tachycardia, can trigger ventricular fibrillation wherein the heart beats chaotically resulting in little or no net flow of blood from the heart to the brain and other organs. Ventricular fibrillation, if not terminated, is fatal. Hence, it is highly desirable to monitor increases in the risk or frequency of arrhythmia, especially in "at-risk" patients, in order to avoid or prevent arrhythmias, particularly ventricular tachycardia.

Many FDA-approved prescription and over-the-counter medications have been found to affect the likelihood and frequency of arrhythmia. Among the medications that may affect the likelihood or frequency of arrhythmia are: antibiotics such as ampicilin, clarithromycin and erythromycin; antidepressants such as Nortriptyline, Doxepin, Amoxapine; antihistamines such as diphenhydramine, and terfenadine; and many others. Many of these medications are prescribed or purchased for reasons unrelated to cardiovascular health. Such, medications may be prescribed by physicians who are unaware of the patient's cardiovascular health. Some such medications may also be bought over-the-counter by a patient without knowledge of the side effects of the medication. Moreover, the arrythmogenic effects of a medication may only appear in certain patients or when administered in combination with other medications. Thus, even where a patient is under treatment for a cardiovascular condition, and possibly at risk for arrhythmia, the patient may inadvertently take medications that increase the risk of arrhythmia. Thus, it would be particularly desirable to monitor any changes in arrhythmia risk related to the administration of medications.

Unfortunately, monitoring of the possible arrythmogenic effects of medications in individual patients is typically ad hoc and relies to a great extent on self-reporting by the patient so that the cardiovascular physician is aware of all medications the patient is taking. Unfortunately, the patient may not be sufficiently aware of changes in arrhythmia risk to report changes to the physician. The patient may also have insufficient knowledge of the side-effects of the medications the patient is taking to believe that they warrant reporting to the physician. The physician may, therefore, be unaware of the need to monitor for changes in the risk of arrhythmia in a particular patient.

One mechanism by which medications may increase the risk of arrhythmia is by prolonging the QT interval. The mechanisms underlying QT prolongation include increased transmural dispersion of repolarization (TDR). TDR is caused by differences in cellular activation and action potential durations through the ventricular wall. Transmural dispersion of repolarization has been shown to be prognostic of arrhythmic risk under a variety of conditions and studies have shown that increased TDR is associated with an increased risk of ventricular tachyarrhythmias. The T-wave of the electrocardiogram ("ECG") is largely the result of voltage gradients created during repolarization of the myocardial cells in the three regions of the transmural wall of the heart (epicardial, mid-myocardial, and endocardial). The T-wave of the ECG is a compound electrical waveform which is the sum of the electrical waveforms resulting from differences in the repolarization time course of the myocardial cells in the three regions of the ventricles. Because the T-wave is generated by repolarization of the cells in the three regions, it is a symbol of transmural dispersion of repolarization. Studies have shown that some morphological parameters of the T-wave of the ECG are sensitive metrics of TDR, including, for example: $T_{apex}$-$T_{end}$ interval, $T_{amplitude}$, $T_{area}$, $T_{slope}$, $T_{morphology}$, and $T_{complexity}$ (as measured by singular value decomposition). See, e.g., C. Antzelevitch, *Cardiac repolarization. The long and short of it*, Europace 7(s2): S3-S9 (2005); F. Akar and D. Rosenbaum, *Transmural Electrophysiological Heterogeneities Underlying Arrhythmogenesis in Heart Failure*, Circ. Res. 93:638-645 (2003); and M. Yamaguchi et al., *T wave peak-to-end interval and QT dispersion in acquired long QT syndrome: a new index for anythmogenicity*, Circulation 110: 904 (2004), all of which are incorporated herein by reference.

However, although TDR has been shown to be prognostic of risk of arrhythmia and analysis of the T-wave of the ECG has been shown to be a sensitive metric of TDR, analyzing T-waves requires long term recording of surface ECGs and off-line analysis. Furthermore, monitoring the ECG requires the use of medical equipment that must be operated by medical personnel in a medical facility such as a physician's office. As stated above, neither the patient nor physician may believe this monitoring is required in any particular case.

Many patients who are at risk for arrhythmia are treated with an implantable cardiac stimulation device such as a pacemaker or implantable defibrillator. An implantable cardiac stimulation device, such as a pacemaker, is implanted within the patient to apply electrical pacing pulses to the heart. For bradycardia, the pacemaker may typically be programmed to pace the heart at a rate of 60 to 80 pulses per minute (ppm) to thereby prevent the heart from beating too slowly and to eliminate any long pauses between heartbeats. To prevent tachyarrhythmias from occurring, the pacemaker can be programmed to overdrive pace the heart at a rate faster than the intrinsic heart rate of the patient. Pacemakers have adjustable parameters which are programmed by the physician in an attempt to provide optimal pacing therapy. However, as described above, the patient may unknowing take medications which affect the patient's risk of arrhythmia. Taking these medications may cause changes in the cardiovascular health of the patient which may warrant reprogramming of the pacemaker. Frequent office visits are required to ensure pacemakers are optimally programmed based on the possible changes in cardiovascular health or other factors. However, even with frequent office visits, the physician cannot be completely assured that the optimal programming is provided at all times between office visits. Hence the patient may not be receiving optimal pacing therapy at all times. Thus, it would be highly desirable if such an implantable cardiac stimulation device could monitor for changes in risk of arrhythmia.

In particular, it would be desirable to have a system that could continuously monitor changes in risk of arrhythmia induced by medications.

It would also be desirable to have a system that could continuously monitor changes in risk of arrhythmia associated with medications without requiring active intervention by physician or patient.

It would further be desirable to have a system that could automatically warn the patient or a physician, nurse or manufacturer if the system detects a dangerous change in the risk of arrhythmia.

It would still further be desirable to have an implantable cardiac stimulation device that could automatically adjust its cardiac rhythm management ("CRM") parameters based on detected changes in risk of arrhythmia.

It would yet further be desirable to have a system that could correlate changes in risk of arrhythmia with the medications taken by the patient in order to modify the medication regimen to reduce the risk of arrhythmia. We should also add using this technique to guide the modification of Rx or make recommendation to the clinician. Also, the technique could be used to monitor if the adjustments made to the medications have made a corresponding beneficial change in TMD. This could be used essentially in a closed loop system. Please add the corresponding paragraph in the spec and add the appropriate claims for these.

SUMMARY OF THE INVENTION

In view of the disadvantages of the state of the art, the present invention provides, in one embodiment, an implantable device which can continuously monitor changes in the risk of arrhythmia induced by medications by analyzing an aspect of T-wave morphology to generate a metric of transmural dispersion of repolarization. The implantable device monitors changes in the risk of arrhythmia without requiring active intervention by physician or patient. The implantable device monitors changes in the metric of transmural dispersion of repolarization as a proxy for the risk of arrhythmia. The implantable device can automatically communicate a warning to the patient or a physician, nurse or manufacturer if the system detects a dangerous change in the risk of arrhythmia. In some embodiments the implantable device forms part of a system for correlating changes in risk of arrhythmia with medications taken by the patient in order to modify the medication regimen to reduce the risk of arrhythmia.

In accordance with a specific embodiment of the present invention an implantable cardiac stimulation device is provided which includes the ability to monitor a metric of transmural dispersion of repolarization derived from a ventricular electrogram ("EGM") to generate an index of change in transmural dispersion of repolarization and thereby track the arrythmogenic side-effects of medications. In this embodiment, the metric of transmural dispersion of repolarization is particularly correlated to ventricular TDR rather than spatial variations in repolarization between the different areas of the heart. By comparing the ventricular metric of transmural dispersion of repolarization at different times, the present invention develops an index of ventricular transmural dispersion of repolarization reflecting changes in ventricular transmural dispersion of repolarization over time. By correlating the index of ventricular transmural dispersion of repolarization with the administration of medication to the patient, the arrythmogenic affects of a medication may be detected and the treatment of a patient may be adjusted to reduce the risk of arrhythmia. The implantable cardiac stimulation device in some embodiments may also automatically adjust its cardiac rhythm management ("CRM") parameters based on detected changes in the risk of arrhythmia.

In a further embodiment of the present invention, the implantable cardiac stimulation device has a circuit for receiving information about the start of medication administration in order to commence recording of a metric of transmural dispersion of repolarization and/or calculation of an index of change in transmural dispersion of repolarization. In another embodiment, the implantable cardiac stimulation device keeps a rolling calculation of a metric of transmural dispersion of repolarization and/or the index of change transmural dispersion of repolarization in memory. The metric of transmural dispersion of repolarization and/or the index of change in transmural dispersion of repolarization may be downloaded by a physician and correlated retrospectively with any changes in medication regimen. In another embodiment of the invention, the implantable cardiac stimulation device may automatically trigger a warning when the index of change in transmural dispersion of repolarization is determined to be outside of acceptable bounds. The warning may be provided directly to the patient or via telemetric and/or wireless communication to a physician, clinician, nurse, caregiver or device manufacturer. In another embodiment of the present invention, the metric of transmural dispersion of repolarization and/or the index of change transmural dispersion of repolarization is transmitted to an external portable device. The external portable device may automatically trigger a warning when the index of change in transmural dispersion of repolarization is determined to be outside of acceptable bounds. The warning may be provided directly to the patient or via wireless communication to a physician, clinician, nurse, caregiver or device manufacturer so that the medication can be stopped or replaced.

In a further embodiment of the present invention, one or more data entry devices are provided for gathering an accurate record of the patient's medication regimen. In one embodiment, medication regimen data entered by the patient, physician or other caregiver is collected in a single database or accessible from a single computer system using a communication network. Analysis of the metric of transmural dispersion of repolarization in comparison to the accumulated medication data may be used to detect and analyze the arrythmogenic affects of a particular medication in the patient's medication regimen. Once the arrythmogenic effects of a medication have been detected and analyzed, appropriate steps may be taken to adjust the medication regimen to reduce or eliminate arrythmogenic effects. In addition, the implantable cardiac stimulation device may be programmed with new cardiac rhythm management ("CRM") settings in light of any changes in risk of arrhythmia.

Thus, various systems and methods are provided for monitoring the arrythmogenic effects of medications by monitoring changes in transmural dispersion of repolarization as a proxy for arrythmogenicity. Other objects, features and advantages of the invention will be apparent from the detailed description to follow.

BRIEF DESCRIPTION OF THE DRAWINGS

The above, and further features, advantages and benefits of the present invention will be apparent upon consideration of the present description taken in conjunction with the accompanying drawings, in which.

DETAILED DESCRIPTION OF THE INVENTION

Figure 1:
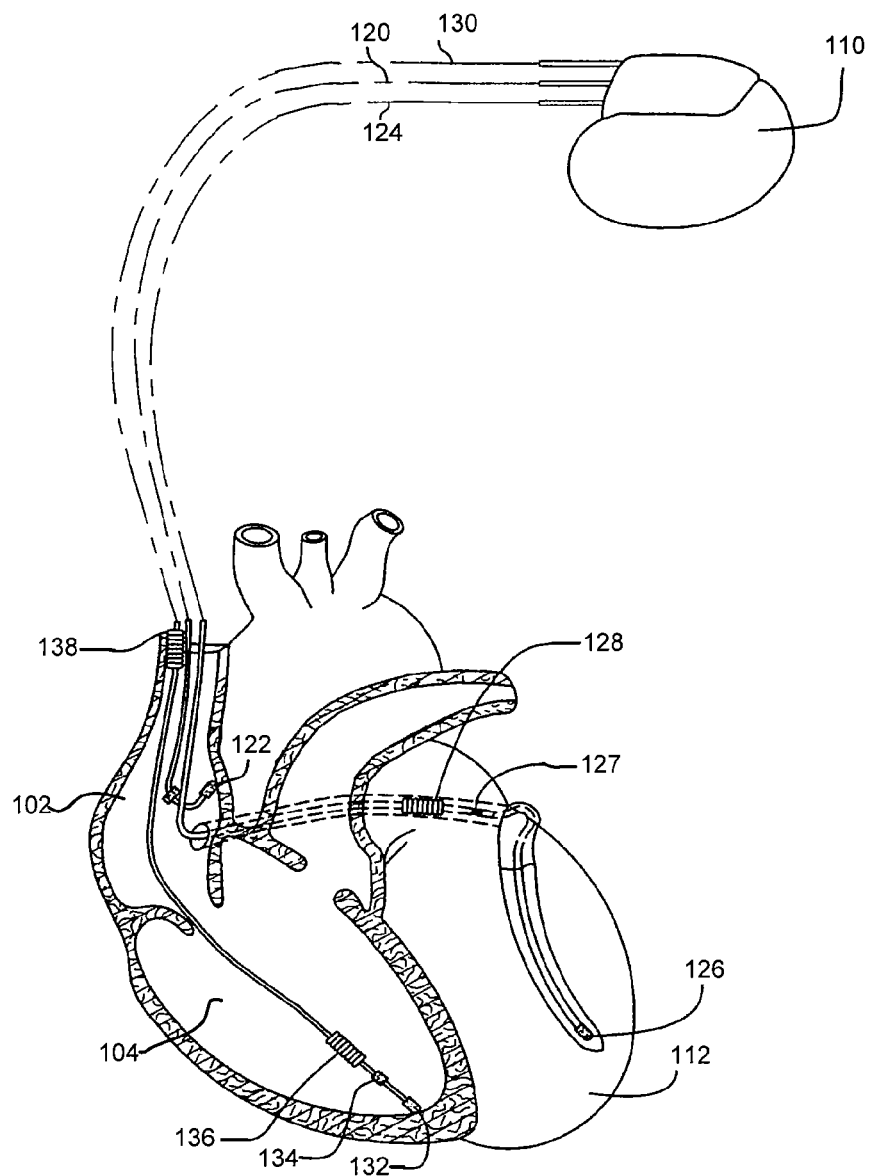
FIG. 1 is a simplified, partly cutaway view illustrating an implantable cardiac stimulation device in electrical communication with at least three leads implanted into a patient's heart for delivering multi-chamber stimulation and shock therapy.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

Implantable Cardiac Stimulation Device

FIG. 1 illustrates an exemplary cardiac stimulation device 110 in electrical communication with a patient's heart 112 by way of three leads 120, 124 and 130 suitable for sensing cardiac electrogram signals and also delivering multi-chamber stimulation and shock therapy. To sense atrial cardiac signals and to provide right atrial chamber stimulation therapy, the cardiac stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the cardiac stimulation device 110 is coupled to a "coronary sinus" lead 124 designed for placement in the "coronary sinus region" via the coronary sinus so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, the coronary sinus lead 124 is designed to receive atrial and ventricular cardiac signals and to deliver left ventricular pacing therapy using at least a left ventricular tip electrode 26, left atrial pacing therapy using at least a left atrial ring electrode 127, and shocking therapy using at least a left atrial coil electrode 128.

The cardiac stimulation device 110 is also shown in electrical communication with the patient's heart 12 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 32 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals, and delivering stimulation in the form of pacing and shock therapy to the right ventricle.

Figure 2:
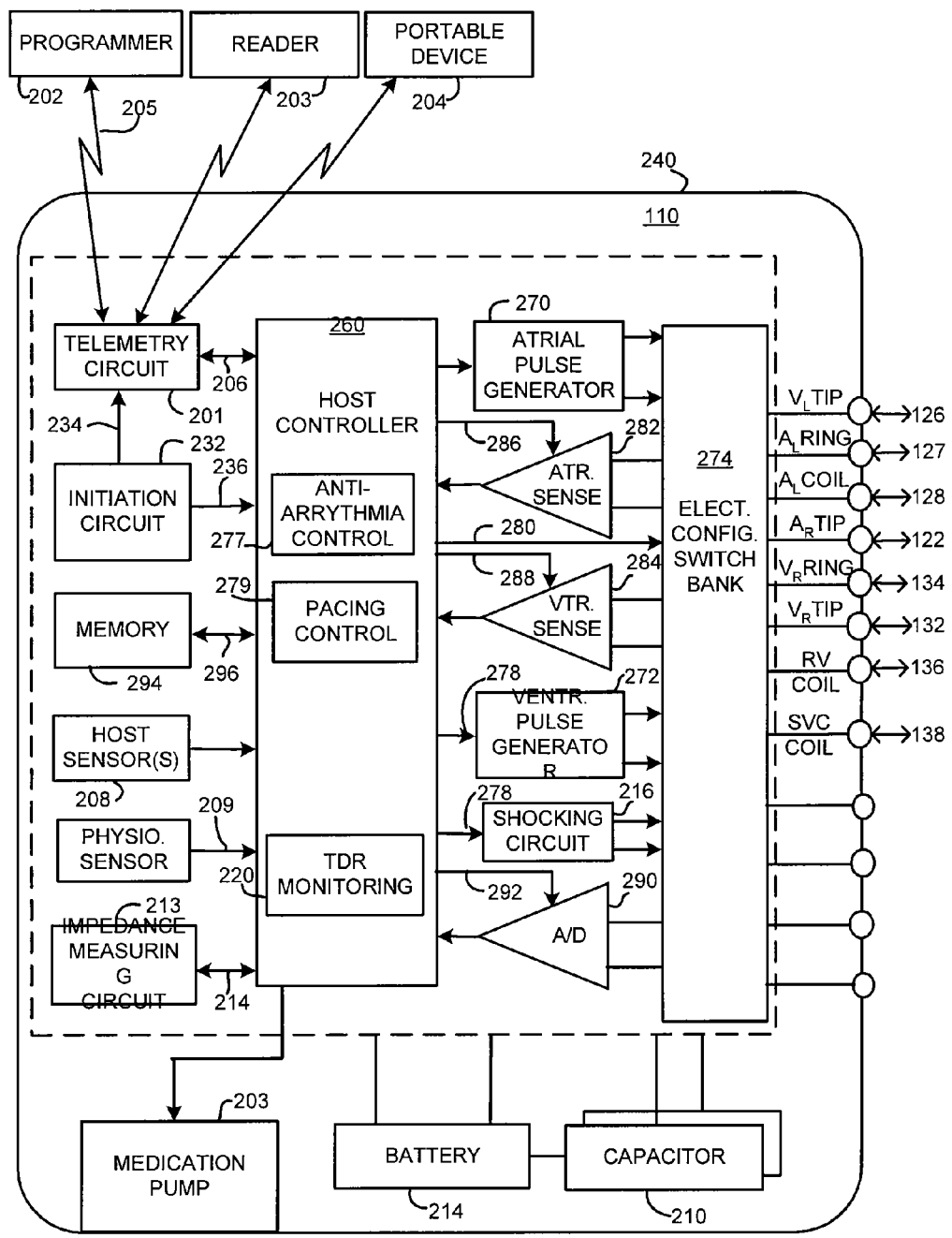
FIG. 2 is a functional block diagram of the multi-chamber implantable cardiac stimulation device of FIG. 1, illustrating the basic elements that provide cardioversion, defibrillation and/or pacing stimulation in four chambers of the heart and particularly illustrating a TDR monitoring unit for monitoring changes in transmural dispersion of repolarization in accordance with one specific embodiment of the present invention.

FIG. 2 illustrates a simplified block diagram of the multi-chamber implantable cardiac stimulation device 110 which is capable of sensing cardiac electrogram signals, monitoring transmural dispersion of repolarization ("TDR") to generate a metric of transmural dispersion of repolarization ("TDRm") and calculate an index of change in transmural dispersion of repolarization ("TDRi"), and also treating both fast and slow arrhythmias with stimulation therapy, including cardioversion, defibrillation, pacing stimulation. While a particular multi-chamber cardiac stimulation device is shown, this is for illustration purposes only and one of skill in the art could readily duplicate, eliminate or disable the appropriate circuitry in any desired combination to provide a device capable of sensing cardiac electrogram signals, monitoring changes in transmural dispersion of repolarization, and, if necessary or desired, treating the appropriate chamber(s) with cardioversion, defibrillation and/or pacing stimulation without departing from the scope of the invention.

Referring to FIG. 2, cardiac stimulation device 110 includes a housing 240 which is often referred to as a "can", "case" or "case electrode", and which may be programmably selected to act as the return electrode for all "unipolar" modes. Housing 240 may be used as a return electrode alone or in combination with one or more of the coil electrodes 128, 136, or 138, for shocking purposes. Housing 240 further includes a connector (not shown) having a plurality of terminals, 242, 244, 246, 248, 252, 254, 256, and 258 (shown schematically and, for convenience, the names of the electrodes to which they are connected are shown next to the terminals).

To achieve right atrial sensing and pacing, the connector includes at least a right atrial tip terminal 242 adapted for connection to the right atrial (AR) tip electrode 122. To achieve left chamber sensing, pacing and/or shocking, the connector includes at least a left ventricular (VL) tip terminal 244, a left atrial (AL) ring terminal 246, and a left atrial (AL) shocking terminal (coil) 248, which are adapted for connection to the left ventricular tip electrode 126, the left atrial ring electrode 127, and the left atrial coil electrode 128, respectively. To support right chamber sensing, pacing and/or shocking, the connector further includes a right ventricular (VR) tip terminal 252, a right ventricular (VR) ring terminal 254, a right ventricular (RV) shocking terminal (coil) 256, and an SVC shocking terminal (coil) 258, which are adapted for connection to the right ventricular tip electrode 132, right ventricular ring electrode 134, the RV coil electrode 136, and the SVC coil electrode 138, respectively.

At the core of cardiac stimulation device 110 is a programmable microcontroller, host controller 260, which controls the various modes of stimulation therapy. As is well known in the art, host controller 260 includes a microprocessor, or equivalent control circuitry or processor, designed for controlling the delivery of stimulation therapy, and may further include RAM or ROM memory, logic and timing circuitry, state machine circuitry, and I/O circuitry. Typically, host controller 260 includes the ability to process or monitor input signals (data) as controlled by program code stored in a designated block of memory. The details of the design and operation of host controller 260 are not critical to the present invention. Rather, any suitable host controller 260 may be used that carries out the functions described herein. The use of microprocessor-based control circuits for performing timing and data analysis functions is well known in the art.

As shown in FIG. 2, an atrial pulse generator 270 and a ventricular pulse generator 272 generate pacing stimulation pulses for delivery by the right atrial lead 120, the right ventricular lead 130, and/or the coronary sinus lead 124 via a switch bank 274. It is understood that in order to provide stimulation therapy in each of the four chambers of the heart, the atrial pulse generator 270 and the ventricular pulse generator 272 may include dedicated, independent pulse generators, multiplexed pulse generators, or shared pulse generators. The atrial pulse generator 270 and the ventricular pulse generator 272 are controlled by host controller 260 via appropriate control signals 276 and 278, respectively, to trigger or inhibit the stimulation pulses.

Host controller 260 further includes pacing control unit 279 which is used to control the timing of such stimulation pulses (e.g., pacing rate, atrio-ventricular (A-V) delay, atrial interconduction (A-A) delay, ventricular interconduction (V-V) delay, pacing mode, etc.), as well as to keep track of the timing of refractory periods, PVARP intervals, noise detection windows, evoked response windows, alert intervals, marker channel timing, etc.

The switch bank 274 includes a plurality of electrically configurable switches for connecting the desired electrodes to the appropriate I/O circuits, thereby providing complete electrode programmability. Accordingly, the switch bank 274, in response to a control signal 280 from host controller 260, determines the polarity of the stimulation pulses (e.g., unipolar, bipolar, combipolar, etc.) by selectively closing the appropriate combination of switches (not shown) as is known in the art. If multiple RV electrodes are employed to generate a single averaged ventricular signal, then switch bank 274 is configured to allow the paralleling (or averaging) of the multiple RV electrodes to simulate a large electrode for accurate sensing of the T-wave.

Atrial sensing circuits 282 and ventricular sensing circuits 284 may also be selectively coupled to the right atrial lead 120, coronary sinus lead 124, and the right ventricular lead 130, through the switch bank 274, for detecting the presence of cardiac activity in each of the four chambers of the heart. Accordingly, the atrial and ventricular sensing circuits 282 and 284 may include dedicated sense amplifiers, multiplexed amplifiers, or shared amplifiers. The switch bank 274 determines the "sensing polarity" of the cardiac signal by selectively closing the appropriate switches. In this way, the clinician may program the sensing polarity independent of the stimulation polarity. Each of the sensing circuits, 282 and 284 preferably employ one or more low power, precision amplifiers with programmable gain and/or automatic gain control, bandpass filtering, and a threshold detection circuit, to selectively sense the cardiac signal of interest. The automatic gain control enables the cardiac stimulation device 110 to deal effectively with the difficult problem of sensing the low amplitude signal characteristics of atrial or ventricular fibrillation.

The outputs of the atrial and ventricular sensing circuits 282 and 284 are connected to host controller 260 for triggering or inhibiting the atrial and ventricular pulse generators 270 and 272, respectively, in a demand fashion, in response to the absence or presence of cardiac activity, respectively, in the appropriate chambers of the heart. The atrial and ventricular sensing circuits 282 and 284, in turn, receive control signals over signal lines 286 and 288 from host controller 260, for controlling the gain, threshold, polarization charge removal circuitry (not shown), and the timing of any blocking circuitry (not shown) coupled to the inputs of the atrial and ventricular sensing circuits 282 and 284.

Cardiac signals are also applied to the inputs of an analog-to-digital (ND) data acquisition system 290. Data acquisition system 290 is configured to acquire intracardiac electrogram signals, convert the raw analog data into digital signals, and store the digital signals for later processing and/or telemetric transmission to an external device 202. Data acquisition system 290 is coupled to the right atrial lead 120, the coronary sinus lead 124, and the right ventricular lead 130 through switch bank 274 to sample cardiac signals across any pair of desired electrodes. Data acquired by data acquisition system 290 (and optionally stored) can be used for subsequent analysis to guide the programming of the device and/or to monitor changes in T-wave morphology, appropriately adjust pacing interval parameters, select optimum pacing intervals, and/or select appropriate anti-arrhythmia therapy.

Advantageously, data acquisition system 290 may be coupled to host controller 260 or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. Host controller 260 detects a depolarization signal during a window following a stimulation pulse, the presence of which indicates that capture has occurred. Host controller 260 enables capture detection by triggering the ventricular pulse generator 272 to generate a stimulation pulse, starting a capture detection window using the timing circuitry within host controller 260, and enabling data acquisition system 290 via control signal 292 to sample the cardiac signal that falls in the capture detection window and, based on the amplitude of the sampled cardiac signal, determines if capture has occurred.

One function of the cardiac stimulation device 110 is to operate as an implantable cardioverter/defibrillator ("ICD") device. That is, cardiac stimulation device 110 detects the occurrence of an arrhythmia, and automatically applies an appropriate electrical shock therapy to the heart aimed at terminating the detected arrhythmia. To this end, anti-arrhythmia control unit 277 of control host controller 260 further controls a shocking circuit 216 by way of a control signal 218. The shocking circuit 216 generates shocking pulses of low (up to 0.5 joules), moderate (0.5-10 joules), or high (11-40 joules) energy, as controlled by host controller 260. Such shocking pulses are applied to the patient's heart through at least two shocking electrodes, as shown in this embodiment, selected from the left atrial coil electrode 128, the RV coil electrode 136, and/or the SVC coil electrode 138 (FIG. 1). As noted above, the housing 140 may act as an active electrode in combination with the RV electrode 136, or as part of a split electrical vector using the SVC coil electrode 138 or the left atrial coil electrode 128 (e.g., using the RV electrode as a common electrode). The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder);

U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

For arrhythmia detection, the anti-arrhythmia control unit 277 of host controller 260 utilizes the atrial and ventricular sensing circuits 282 and 284 to sense cardiac signals, for determining whether a rhythm is physiologic or pathologic. The timing intervals between sensed events (e.g., P-waves, R-waves, and depolarization signals associated with fibrillation which are sometimes referred to as "F-waves" or "Fibwaves") are then classified by anti-arrhythmia control unit 277 of host controller 260 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Host controller 260 is further coupled to a memory 294 by a suitable data/address bus 296, where the programmable operating parameters used by host controller 260 are stored and modified, as required, in order to customize the operation of the cardiac stimulation device 110 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the patient's heart 112 within each respective tier of therapy. A feature of the cardiac stimulation device 110 is the ability to sense and store a relatively large amount of data (e.g., from data acquisition system 290), which data may then be used for subsequent analysis such as, monitoring changes in transmural dispersion of repolarization ("TDR") and also guiding the programming of the cardiac stimulation device 110.

Advantageously, the operating parameters of the cardiac stimulation device 110 may be non-invasively programmed into the memory 294 through a telemetry circuit 201 in telemetric communication with an external programmer 202, such as a, transtelephonic transceiver, or a diagnostic system analyzer. Additionally, telemetry circuit 201 may be used to activate TDR monitoring in association with a change in medication regimen. Telemetry circuit 201 is activated by the microcontroller by a control signal 206. Telemetry circuit 201 advantageously allows EGM, TDRm, TDRi, stroke volume, heart rate, other measured physiological variables and status information relating to the operation of the cardiac stimulation device 110 (as contained in host controller 260 and/or memory 294) to be sent to an external device such as programmer 202, reader 203, or portable device 204 through an established communication link 205. Typically the communication link 205 can only operate between telemetry circuit 201 and one of programmer 202, reader 203, or portable device 204 at any one time. A handshake signal sent from the external device to the telemetry circuit may be used to identify the particular device with which the telemetry circuit 201 is in communication thereby defining what operations may be performed by the device. For example, programming of cardiac stimulation device 110 should only be permitted by programmer 202 under the control of a physician as described in more detail with respect to FIG. 3. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (note: this relates to transfer of EGM data) (McClure et al.), which patents are hereby incorporated herein by reference.

Cardiac stimulation device 110 further includes initiation circuit 232. Initiation circuit 232 may comprise magnet detection circuitry. Initiation circuit 232 is coupled to host controller 260 by connection 236 and/or to telemetry circuit 201 by connection 234. The purpose of the initiation circuit is to detect an initiation signal from outside the patient. For example, a magnet placed over the cardiac stimulation device 110 may be used as the initiation signal, which signal may be used by a clinician to initiate various test functions of the cardiac stimulation device 110 and/or to signal host controller 260 that an external programmer 202 is in place to receive or transmit data to host controller 260 through the telemetry circuit 201. Initiation circuit 232 may also be used to activate TDR monitoring in association with a change in medication regimen.

A TDR monitoring unit 220 of host controller 260 processes EGM signals to monitor changes in transmural dispersion or repolarization. TDR monitoring unit 220 analyzes EGM signals to calculate a metric representative of TDR ("TDRm"). TDR monitoring unit 220 may receive different EGM signals from different leads and may process each separately to generate a TDRm value for each electrode. If multiple TDRm values are calculated, the TDRm values may be recorded separately or combined into a single metric. Alternatively, the EGM waveforms from a combination of electrodes may be combined prior to analysis by TDR monitoring unit 220 and a TDRm value calculated from the combined waveform. After calculation, the metric of TDR is stored in host controller 260 and/or memory 294. The TDR monitoring unit 220 utilizes the current TDRm and one or more prior TDRm values stored in memory to calculate an index of change in transmural dispersion of repolarization ("TDRi"). In a general embodiment TDRi is calculated by comparing the current value of TDRm with the TDRm measured for a prior time period. TDRi is used to monitor the arrythmogenic effects of medications in accordance with an embodiment of the invention. The calculation of TDRm and TDRi by TDR monitoring unit 220 is described in detail below with respect to FIG. 6.

If a medication pump 203 is provided, TDR monitoring unit 220 may be used to send control signals to the medication pump for adjusting the amount of medication delivered to the patient in view of the determined TDRi or arrythmogenicity. Information regarding implantable medication pumps may be found in U.S. Pat. No. 4,731,051 to Fischell and in U.S. Pat. No. 4,947,845 to Davis, both of which are incorporated by reference herein. The medication pumps discussed therein, or other suitable medication pumps, may be modified as needed to permit receipt of control signals from TDR monitoring unit 220.

Cardiac stimulation device 110 additionally includes a power source such as a battery 210 that provides operating power to all the circuits shown in FIG. 2. For a cardiac stimulation device 110, which employs shocking therapy, the battery 210 must be capable of operating at low current drains for long periods of time and also be capable of providing high-current pulses (for charging capacitor 210) when the patient requires a shock pulse. Battery 210 must preferably have a predictable discharge characteristic so that elective replacement time can be detected. Accordingly, cardiac stimulation device 110 can employ lithium/silver vanadium oxide batteries.

Programmer

Figure 3:
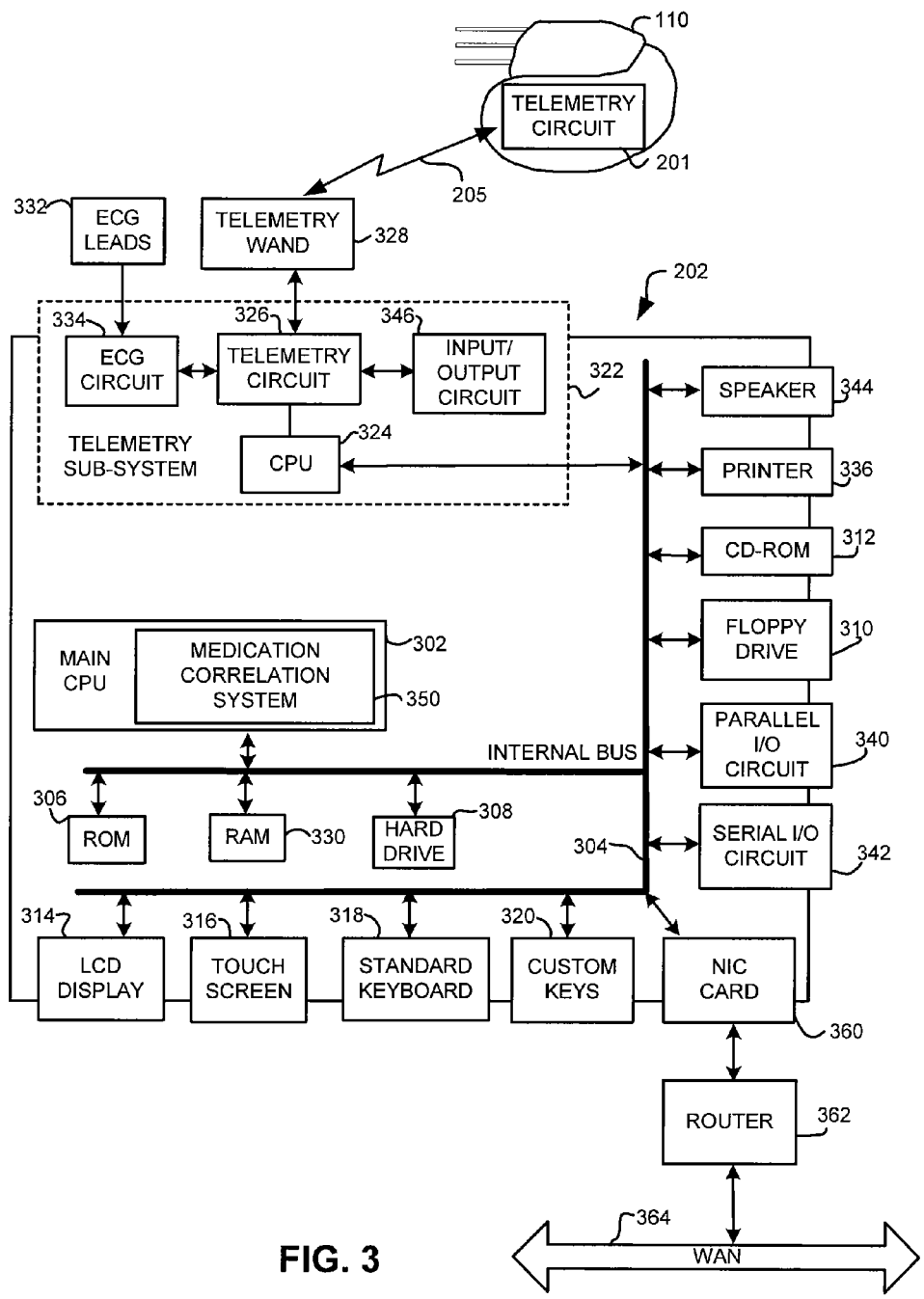
FIG. 3 is a functional block diagram illustrating components of a programmer for use in programming the implantable cardiac stimulation device of FIGS. 1 and 2, and illustrating a medication correlation unit for use in correlating changes in transmural dispersion of repolarization with changes in a patient's medication regimen.

FIG. 3 illustrates pertinent components of a programmer 202 for use in programming an implantable cardiac stimulation device which has a system which can monitor changes in arrythmogenic risk associated with medications. Briefly, programmer 202 permits a physician or other authorized user to program the operation of the implantable cardiac stimulation device 110 and to retrieve and display information received from the implantable cardiac stimulation device 110 such as TDRi, measured physiological variables data, EGM data and device diagnostic data. Additionally, programmer 202 may receive and display ECG data from separate external ECG leads that may be attached to the patient. Programmer 220 is capable of receiving TDRm and/or TDRi data from cardiac stimulation device 110 and communicating a warning to a physician or other authorized user if TDRi is outside of acceptable bounds. Depending upon the specific programming of the programmer, programmer 202 may also be capable of processing and analyzing data received from the implantable cardiac stimulation device 110 and from ECG leads 332 to, for example, render preliminary diagnosis as to medical conditions of the patient or to the operations of the implantable cardiac stimulation device 110.

Now, considering the components of programmer 202 by reference to FIG. 3, operations of programmer 202 are controlled by a CPU 302, which may be a generally programmable microprocessor or microcontroller or may be a dedicated processing device such as an application specific integrated circuit (ASIC) or the like. Software instructions to be performed by the CPU are accessed via an internal bus 304 from a read only memory (ROM) 306 and random access memory 330. Additional software may be accessed from a hard drive 308, floppy drive 310, and CD ROM drive 312, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 314 or other suitable computer display device. To this end, the CPU may, for example, display a menu of specific programming parameters of the implantable cardiac stimulation device 110 to be programmed or may display a menu of types of diagnostic data to be retrieved and displayed. In response thereto, the physician enters various commands via either a touch screen 316 overlaid on LCD display 314 or through a standard keyboard 318 supplemented by additional custom keys 320, such as an emergency VVI (EVVI) key. The EVVI key sets the implantable cardiac stimulation device 110 to a safe VVI mode with high pacing outputs. This ensures life sustaining pacing operation in nearly all situations but by no means is it desirable to leave cardiac stimulation device 110 in the EVVI mode at all times.

Typically, the physician initially controls programmer 202 to retrieve data stored within the implanted medical device and to also retrieve ECG data from ECG leads 332, if any, coupled to the patient. To this end, CPU 302 transmits appropriate signals to a telemetry circuit 322, which provides components for directly interfacing with implantable cardiac stimulation device 110, and ECG leads 332. Telemetry subsystem 322 includes its own separate CPU 324 for coordinating the operations of the telemetry subsystem. Main CPU 302 of programmer communicates with telemetry subsystem CPU 324 via internal bus 304. Telemetry subsystem 322 additionally includes a telemetry circuit 326 connected to a telemetry wand 328, which cooperate to receive and transmit signals electromagnetically from telemetry circuit 201 of the implantable cardiac stimulation device 110. Telemetry wand 328 is placed over the chest of the patient near the implanted cardiac stimulation device 110 to permit reliable transmission of data, over telemetric link 205, between the telemetry wand and the implantable cardiac stimulation device 110. Typically, at the beginning of the programming session, the external programming device controls the implantable cardiac stimulation device 110 via appropriate signals generated by telemetry wand 328 to output all previously recorded patient and device diagnostic information. Patient diagnostic information includes, for example, stored TDRm data, stored TDRi data, measured physiological variables data, recorded EGM data and statistical patient data such as the percentage of paced versus sensed heartbeats. Device diagnostic data includes, for example, information representative of the operation of the implantable cardiac stimulation device 110 such as lead impedances, battery voltages, battery recommended replacement time (RRT) information and the like. Data retrieved from the implantable cardiac stimulation device 110 is stored by external programmer 302 either within a random access memory (RAM) 330, hard drive 308 or within a floppy diskette placed within floppy drive 310. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implantable cardiac stimulation device 110 is transferred to programmer 302, the implantable cardiac stimulation device 110 may be further controlled to transmit additional data in real time as it is detected by the implantable cardiac stimulation device 110, such as additional TDRm data, TDRi data, measured physiological variables data, EGM data, lead impedance data, and the like. Additionally, telemetry subsystem 322 may receive ECG signals from ECG leads 332 via an ECG processing circuit 334. As with data retrieved from the implantable cardiac stimulation device 110 itself, signals received from the ECG leads 332 are stored within one or more of the storage devices of programmer 202. Typically, ECG leads 332 output analog electrical signals representative of the ECG. Accordingly, ECG circuit 334 includes analog to digital conversion circuitry for converting the signals to digital data appropriate for further processing within programmer 202. Depending upon the implementation, the ECG circuit may be configured to convert the analog signals into event-record data for ease of processing along with the event-record data retrieved from the implantable cardiac stimulation device 110. Typically, signals received from the ECG leads 332 are received and processed in real time.

Programmer 202 also includes a network interface card ("NIC") 360 to permit transmission of data to and from other computer systems via a router 362 and wide area network ("WAN") 364. Alternatively, programmer 202 might include a modem for communication via the public switched telephone network (PSTN). Depending upon the implementation, the modem may be connected directly to internal bus 304 may be connected to the internal bus via either a parallel port 340 or a serial port 342. Data transmitted from other computer systems may include, for example, data regarding medication prescribed, administered or sold to the patient. This medication data may be provided by the patient, physicians, nurses, caregivers, pharmacies, medical insurance companies and the like as described in more detail with respect to FIG. 4.

CPU 302 includes a medication correlation unit 350 for detecting and analyzing the arrythmogenic effects of a medication or a medication regimen administered to the patient and issuing warnings to the physician or other authorized user of programmer 202. Data for the operation of medication correlation unit 350 is derived by correlating TDRm and TDRi values transmitted from cardiac stimulation device 110 via telemetry wand 328 with data regarding the medication or medication regimen administered to the patient. This medication data may be provided by the patient, physicians, nurses, caregivers, pharmacies, medical insurance companies and the like. This information can be entered directly into programmer 202 or entered in other computer systems and transferred to or accessed by programmer 202 over WAN 364 as described in more detail with respect to FIG. 4. The medication correlation unit 350 allows the physician to compare the medication history of the patient with TDR values and TDRi values from the implantable cardiac stimulation device 110 and thus evaluate the arrythmogenic effects of any medication. The operation of medication correlation unit 350 is described in detail below with reference to FIG. 7.

Thus, programmer 202 receives data both from implantable cardiac stimulation device 110, from external ECG leads 332, and medication data from a number of possible sources. Data retrieved from the implantable cardiac stimulation device 110 includes parameters representative of the current programming state of the implantable cardiac stimulation device 110. Under the control of the physician, programmer 202 displays the current programming parameters and permits the physician to reprogram the parameters. To this end, the physician enters appropriate commands via any of the aforementioned input devices and, under control of CPU 302, the programming commands are converted to specific programming parameters for transmission to the implantable cardiac stimulation device 110 via telemetry wand 328 to thereby reprogram the implantable cardiac stimulation device 110. Prior to reprogramming specific parameters, the physician may control the external programmer to display any or all of the data retrieved from the implantable cardiac stimulation device 110 or from the ECG leads, including displays of ECGs, EGMs, TDRm, TDRi, medication data and statistical patient information. Any or all of the information displayed by programmer 202 may also be printed using a printer 336.

A speaker 344 is included for providing audible tones to the user, such as a warning beep in the event improper input is provided by the physician. Telemetry subsystem 322 may additionally include an input/output circuit 346 which can control the transmission of analog output signals, such as ECG signals output to an ECG machine or chart recorder. Other peripheral devices may be connected to the external programmer via parallel port 340 or a serial port 342 as well. Although one of each is shown, a plurality of input output (10) ports might be provided.

With programmer 202 configured as shown, a physician or other authorized user can retrieve, process and display a wide range of information received from the ECG leads or from the implantable cardiac stimulation device 110 and reprogram the implantable cardiac stimulation device 110 if needed. The descriptions provided herein with respect to FIG. 3 are intended merely to provide an overview of the operation of programmer 202 and are not intended to describe in detail every feature of the hardware and software of the device and are not intended to provide an exhaustive list of the functions performed by the device.

Communication Network

Figure 4:
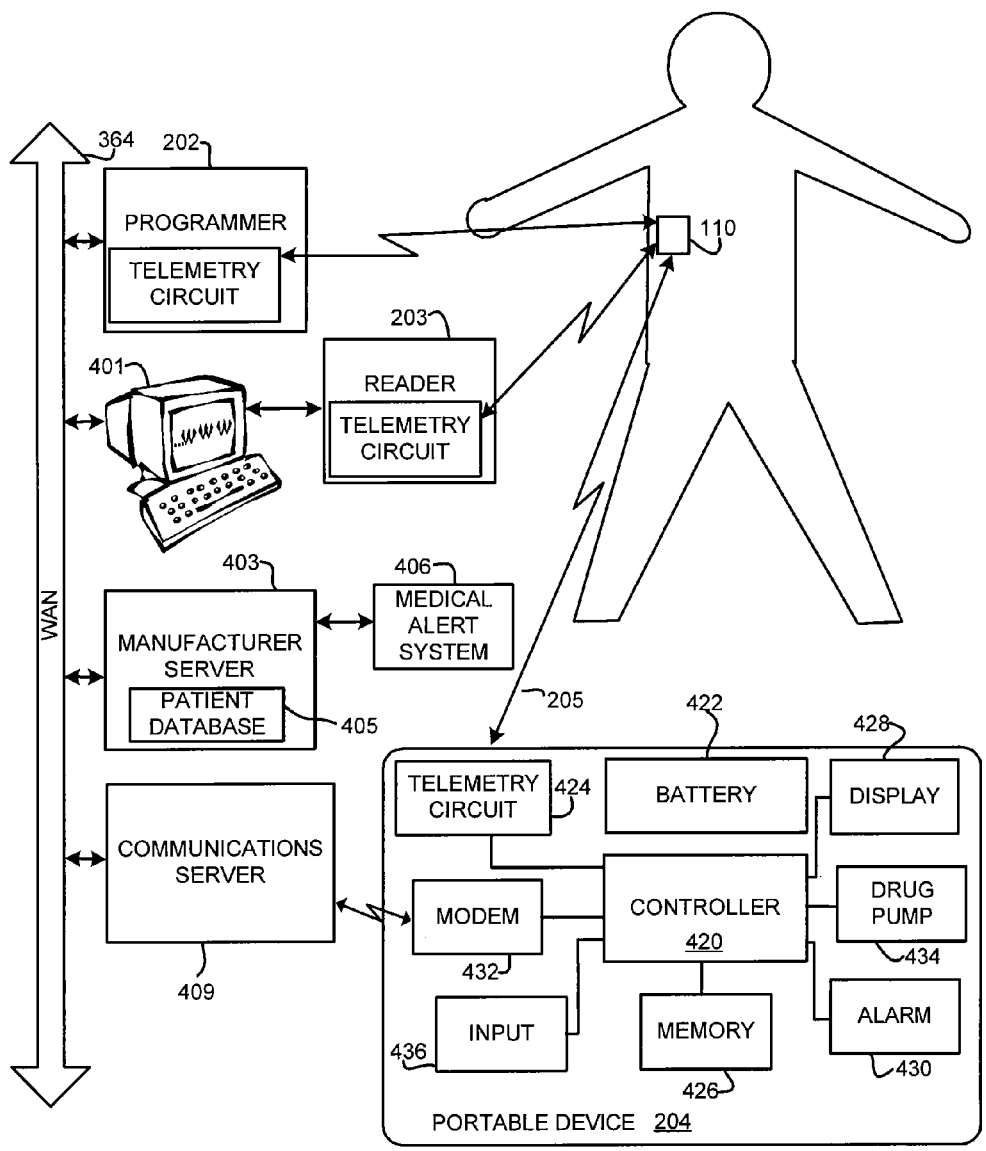
FIG. 4 shows a network communication system with external data entry devices for use with the implantable cardiac stimulation device of FIG. 3 in accordance with one specific embodiment of the present invention.

Referring now to FIG. 4, where a network comprised of the cardiac stimulation device 110 and a number of devices with which it may communicate are shown. As previously discussed, cardiac stimulation device 110 may communicate via telemetry circuit 201 with programmer 202. In addition, the patient may be provided with a reader 203 which has its own telemetry circuit which may receive information from cardiac stimulation device 110. Reader 203 may be, for example, a peripheral device connected to a patient's general purpose computer. Computer system 401 preferably comprises software for initiating transfer of data via reader 203 from cardiac stimulation device 110. The software should also be able to accept data input by the patient using a standard computer keyboard. For example, the patient might be required to keep a diary of medication taken and qualitative feelings of healthfulness. This patient-entered information may be correlated with TDRm and/or TDRi and other physiological data downloaded from cardiac stimulation device 110. Based on TDRm and/or TDRi the computer system may provide a warning to the patient to contact his cardiovascular physician. In addition, computer system 401, if provided with a modem or NIC, can communicate the patient-entered medication data and downloaded TDRm and TDRi data via Wide Area network (WAN) 364 to the computer system of a physician, healthcare provider, or the manufacturer of the cardiac stimulation device 110. One way to achieve this is for computer system 401 to communicate the data to manufacturer server 403. Manufacturer server 403 includes a patient database 404 which provides information regarding the patient and cardiac stimulation device 110, including communication addresses for the physicians, healthcare providers and caregivers of the patient. Manufacturer server 403 can then forward the data to the individuals identified in the patient database via WAN 364. For example, the data may be forwarded to programmer 202 under the control of a physician where the data can be used to readjust the programmed parameters of cardiac stimulation device 110 upon the patient's next visit to the physician. In addition, should the data indicate a serious and immediate problem, manufacturer server 403, may instead communicate the data and patient data to medical alert system 406 which may act by multiple communication channels, such as paging, telephone etc to contact the physician, clinician, nurse, or caregiver of the patient to alert them of said serious an immediate problem or contact emergency services.

Alternatively or additionally, the patient may carry portable device 204. Portable device 204 may have the same general components as a wireless PDA with the addition of a telemetry circuit 424 for receiving information from cardiac stimulation device 110. As shown in FIG. 4, portable device 204 comprises a controller 420, battery 422, telemetry circuit 424, memory 426, input 436, display 428, alarm 430, and wireless modem 432. Portable device 204 may also include or control an external medication pump 434 for supplying e.g. medication to the patient if the patient does not have an implantable medication pump.

Portable device 204 is carried by the patient close to cardiac stimulation device 110 to allow for reliable communication with cardiac stimulation device 110 via telemetry circuit 424. The communication may be initiated by the portable device or by cardiac stimulation device 110. The communication may be initiated with or without user intervention. TDRi. TDRm and other physiological data may be downloaded from cardiac stimulation device 110 to portable device 204. In addition, portable device 204 preferably comprises input means 436, such as a keyboard or touch screen, by which the patient may enter medication data and subjective health data. The downloaded and patient-entered data may then be transmitted via the wireless modem to a communication server 409 and thence via WAN 364 to the manufacturer server 405. This data may be forwarded by manufacturer server 403 in the same way as previously discussed with respect to computer system 401. Additionally, portable device 204 may utilize the TDRm or TDRi data to initiate a warning to the patient if TDRi is outside of acceptable bounds. The warning, may for example, advise the patient to contact their cardiovascular physician. To facilitate such a warning, portable device 204 is preferably provided with an alarm 430 which is a device such as a vibrator, beeper or flashing light to draw attention of the patient to the portable device.

Monitoring Transmural Dispersion of Repolarization

Figure 5:
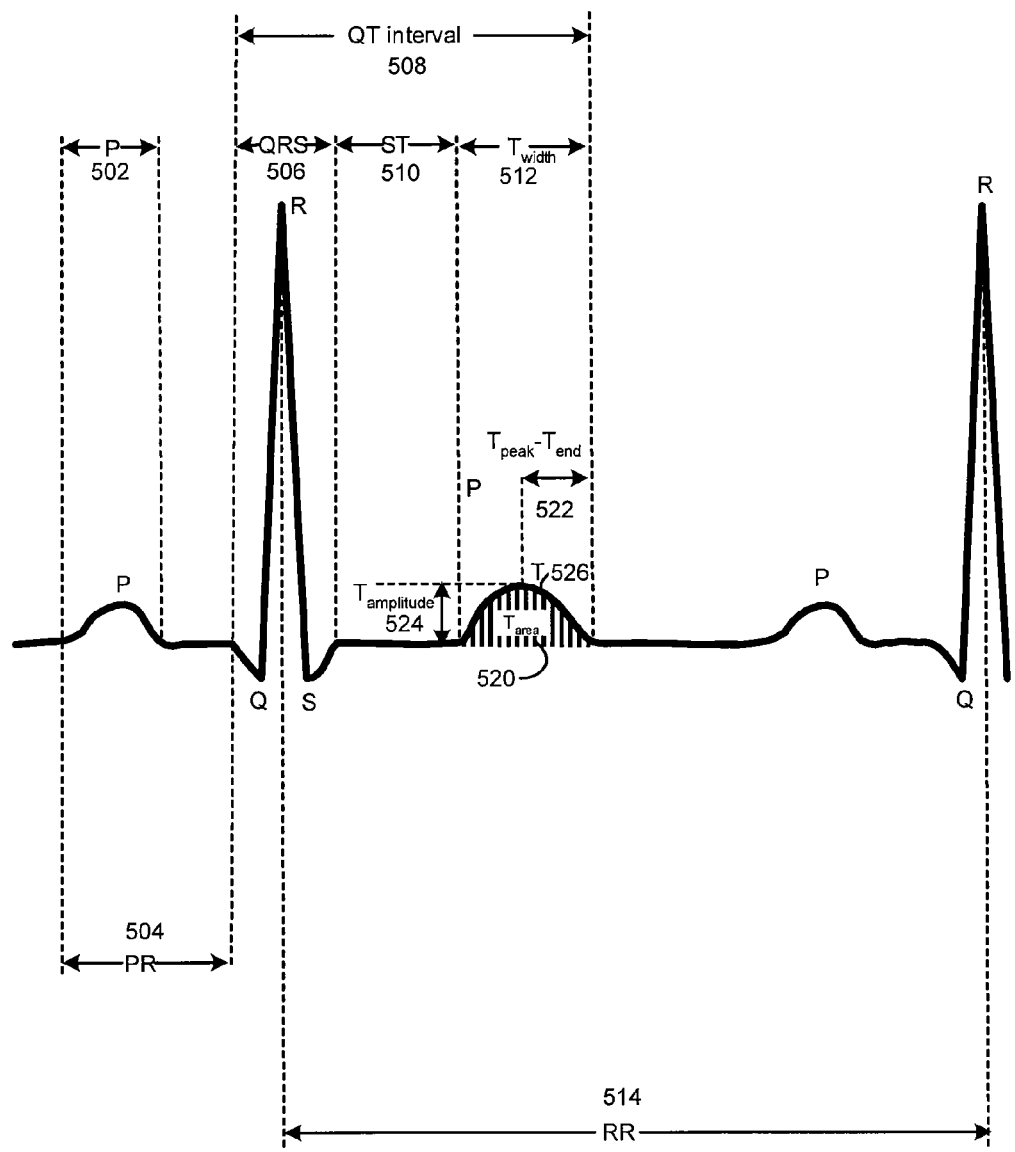
FIG. 5 shows a cardiac EMG trace illustrating components of the cardiac EMG waveform.

TDR monitoring unit 220 of host controller 260 processes cardiac EGM signals to monitor changes in transmural dispersion of repolarization. In a particular embodiment of the invention, TDR monitoring unit 220 analyzes one or more attributes of the T-wave of the EGM in order to calculate a metric of transmural dispersion of repolarization ("TDRm"). FIG. 5 shows a diagram of a cardiac electromyogram ("EMG") waveform. The cardiac EMG is a graphical representation of the electrical activity of the heart as detected by implanted electrodes. The waveform is made up of a number of intervals including the P-wave 502, P-R Segment 504, QRS Complex 506, QT interval 508, ST segment 510, and T-wave 526. The T-wave is identified as the first deflection in the cardiac EMG following the QRS complex, representing ventricular repolarization. However, the term "T-wave" as used herein may refer to a portion of the ventricular QRS-T-wave complex that includes the T-wave and/or the QRS-T segment. For example, one attribute of the T-wave as used herein is the QT interval 508 which is measured from the beginning of the QRS complex to the end of the T-wave.

Figure 6:
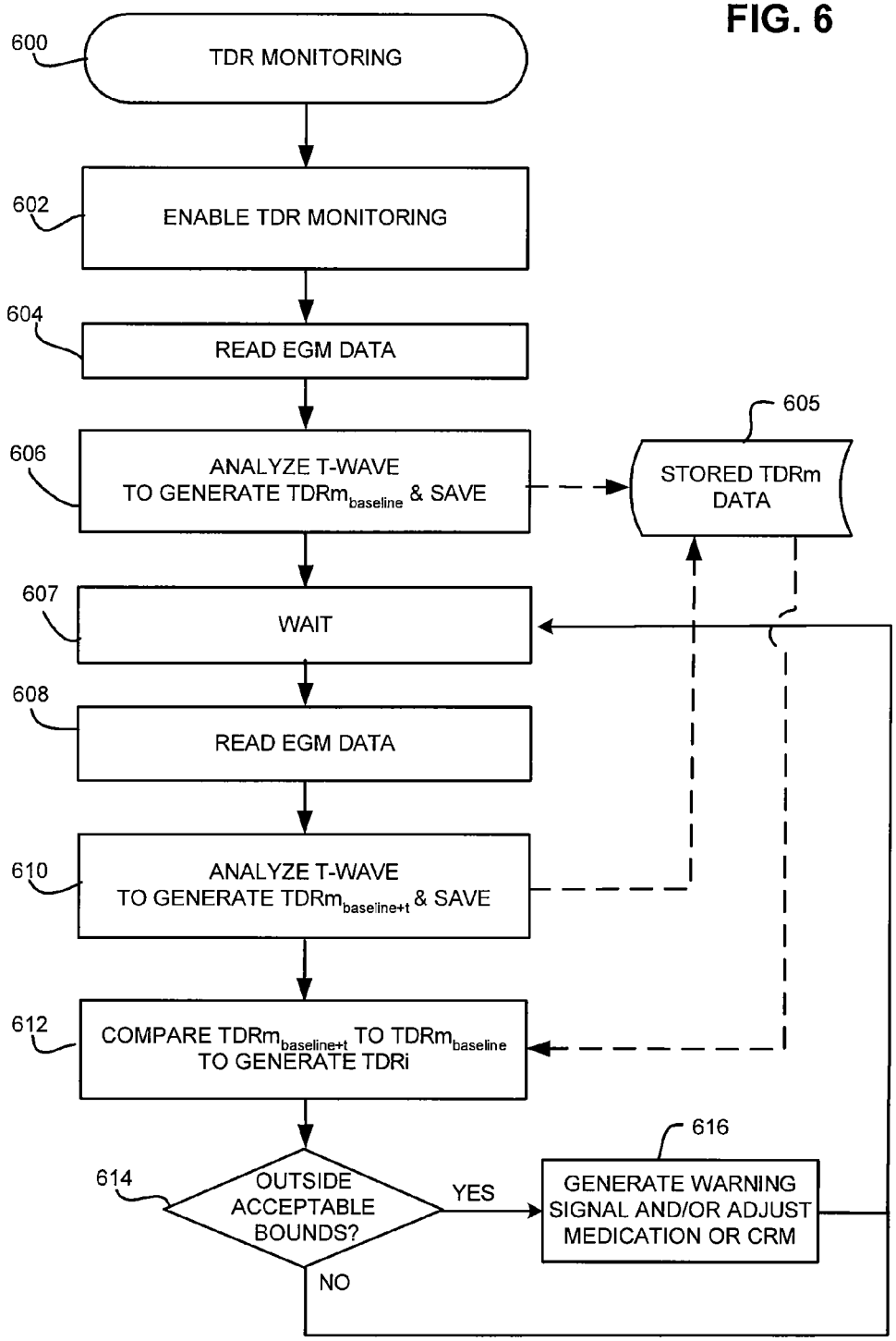
FIG. 6 is a flow diagram illustrating a method performed by the TDR monitoring unit of FIG. 2 to determine a metric of transmural dispersion of repolarization and calculate an index of change in transmural dispersion of repolarization in accordance with one specific embodiment of the present invention.

In order to monitor changes in transmural dispersion of repolarization, TDR monitoring unit 220 generates a metric of TDR ("TDRm"). Any of the metrics of transmural dispersion of repolarization known in the art may be used in accordance with the present invention. Sensitive metrics of TDR may be obtained from one or more of the morphological parameters of T-waves using methods known in the art. The metric of TDR can be, for example, any one of or combination of the following T-wave morphological parameters: $T_{amplitude}$, $T_{peak}$-$T_{end}$, $T_{slope}$, $T_{area}$, $T_{width}$, $T_{timing}$, $T_{morphology}$, QT interval, evoked QT interval, and $T_{complexity}$ (as measured by singular value decomposition) which can all be measured from EGM signals using methods known in the art. Referring again to FIG. 5, the following T-wave morphological parameters are illustrated: $T_{width}$ 512, $T_{area}$ 520, $T_{peak}$-$T_{end}$ 522, QT interval 508, and $T_{amplitude}$ 524. For example, the $T_{peak}$-$T_{end}$ interval 522 has been shown in studies to provide a metric of TDR prognostic of arrhythmic risk. To enhance the calculation of the chosen metric, the chosen T-wave morphological parameter may be measured over a predetermined number of beats (e.g., 2 to 10 beats). Alternatively, the current value of TDRm can be calculated as a running average of its value over a certain time period which can be as long as 24 hrs. Alternatively, the current value of the TDRm can be calculated periodically (hourly/daily/bi-weekly), as an average representative of that period. However, the precise method used to generate TDRm is not important so long as the metric correlates well with transmural dispersion of repolarization and TDRm is measured and stored with sufficient accuracy and frequency to detect changes in TDRm over time. In one embodiment of the present invention, TDRm is monitored as shown in FIG. 6.

Whatever metric is used to calculate TDRm, an index of TDR ("TDRi") is calculated by comparing a value of TDRm measured for one time period with a value of TDRm measured for a prior time period. A time period may include one TDRm measurement or multiple TDRm measurements in which case an average of the TDRm measurements in the time period may be used in the comparison. In certain embodiments a baseline value will be stored at the time that TDR monitoring is commenced coincident with commencing administration of a medication). TDRi can then be calculated by comparing the current value of TDRm with the baseline value of TDR. To assist in explanation, values of TDRm may be identified as $TDRm_t$ where "t" is indicative of the time for which the metric was calculated. A special example of $TDRm_t$ is $TDRm_{baseline}$ which is the value of TDRm when TDR monitoring is initiated. Time ("t") may be indicated relative to initiation of TDR monitoring. For example, $TDRm_{baseline+24\,hr}$ means the TDRm value calculated for a time period 24 hours after the timer period for which $TDRm_{baseline}$ was calculated. In one embodiment, TDRi may be calculated by comparing $TDRm_{baseline+t}$ to $TDR_{baseline}$ and determining the percentage change in TDRm between the time periods. Thus, in this embodiment: TDRi=100* $(TDRm_{baseline+t}-TDR_{baseline})/TDR_{baseline}$ %. Alternatively, or in addition, TDRi may be calculated by determining the percentage change in TDRm per day. Thus, in this embodiment: TDRi=100*$(TDRm_{baseline+t\,days}-TDR_{baseline})/(t*TDR_{baseline})$ % per day.

TDRm is useful as a proxy for risk of arrhythmia and thus TDRi can be monitored over time to monitor changes in the risk of arrhythmia. If TDRi reaches a threshold, TDR monitoring unit 220 can trigger an alert to notify the patient and/or physician so that the medication can be stopped or replaced. In certain embodiments it may be desirable to calculate both TDRi and TDRi/day and have a threshold or thresholds for each index. Thus, an alert may be triggered if either the total increase in arrhythmia risk or the rate of increase in arrhythmia risk is outside of acceptable bounds. In one embodiment of the present invention, TDRi is calculated as shown in FIG. 6.

In a specific embodiment of the invention, $T_{area}$ may be used as the metric of TDR used to calculate TDRi. $T_{area}$ 520 is the area under the T-wave as illustrated in FIG. 5. In order to calculate $T_{area}$, TDR monitoring unit 220 can find the location of the T-wave by detecting the R-wave using standard techniques known in the art. TDR monitoring unit can then identify the maximum value of the EGM signal in an m msec window that occurs following the R-wave or a certain % of cycle length after the R wave. TDR monitoring unit 220 can then determine the amplitude and timing of the T-wave and calculates $T_{area}$. To enhance accuracy, the baseline value of TDRm can be calculated as an average value of $T_{area}$ in a window of N beats. TDR monitoring unit 220 uses a comparison of current value of $T_{area}$ to its previously calculated value or the baseline value to generate TDRi. Specifically, the percentage change in $T_{area}$ from baseline and/or the rate of percentage change in $T_{area}$ may be used as the TDRi to monitor arrythmogenicity of a medication.

In another embodiment of the invention, QT interval 508 may be used as a metric of TDR. The QT interval is measured from the beginning of the QRS complex to the end of the T-wave as illustrated in FIG. 5. To determine QT interval, TDR monitoring unit 220 can detect the R-waves using standard techniques known in the art and then finds the location of the T-wave by identifying the maximum value of the EGM signal in an m msec window that occurs following the R-wave or a certain % of cycle length after the R wave. TDR monitoring unit 220 can then determine the timing of the T-wave and measures the QT interval. TDR monitoring unit 220 can then correct the measured QT interval for heart rate. QT interval may be corrected for heart rate using various formulae such as Bazett's formula: $QTc=QT/\sqrt{RR}$ where QTc is the QT interval corrected for rate, QT is the measured QT interval (in seconds) and RR is the measured interval from the onset of one QRS complex to the onset of the next QRS complex (measured in seconds). To enhance accuracy, QTc can be calculated as the average value of QTc in a window of N beats. TDR monitoring unit 220 uses a comparison of current value of QTc to its previously calculated value or a baseline value of QTc to generate TDRi. Specifically, the percentage change in QTc from baseline and/or rate of percentage change in QTc may be used as the TDRi to monitor arrythmogenicity.

In alternative embodiments, TDRi can be monitored over time to monitor reductions in the risk of arrhythmia for example in connection with the administration of medications intended to ameliorate risk of arrhythmia in the patient. TDRm and TDRi are calculated in the same ways previously described, however, the expectation is that TDRm and TDRi will show a reduction in TDR over time following administration of the medication. If administration of the medication does not correlate with the expected reduction in the patient's risk of arrhythmia, the physician may be advised to change the dosage of a medication or change to an alternative medication.

Figure 7:
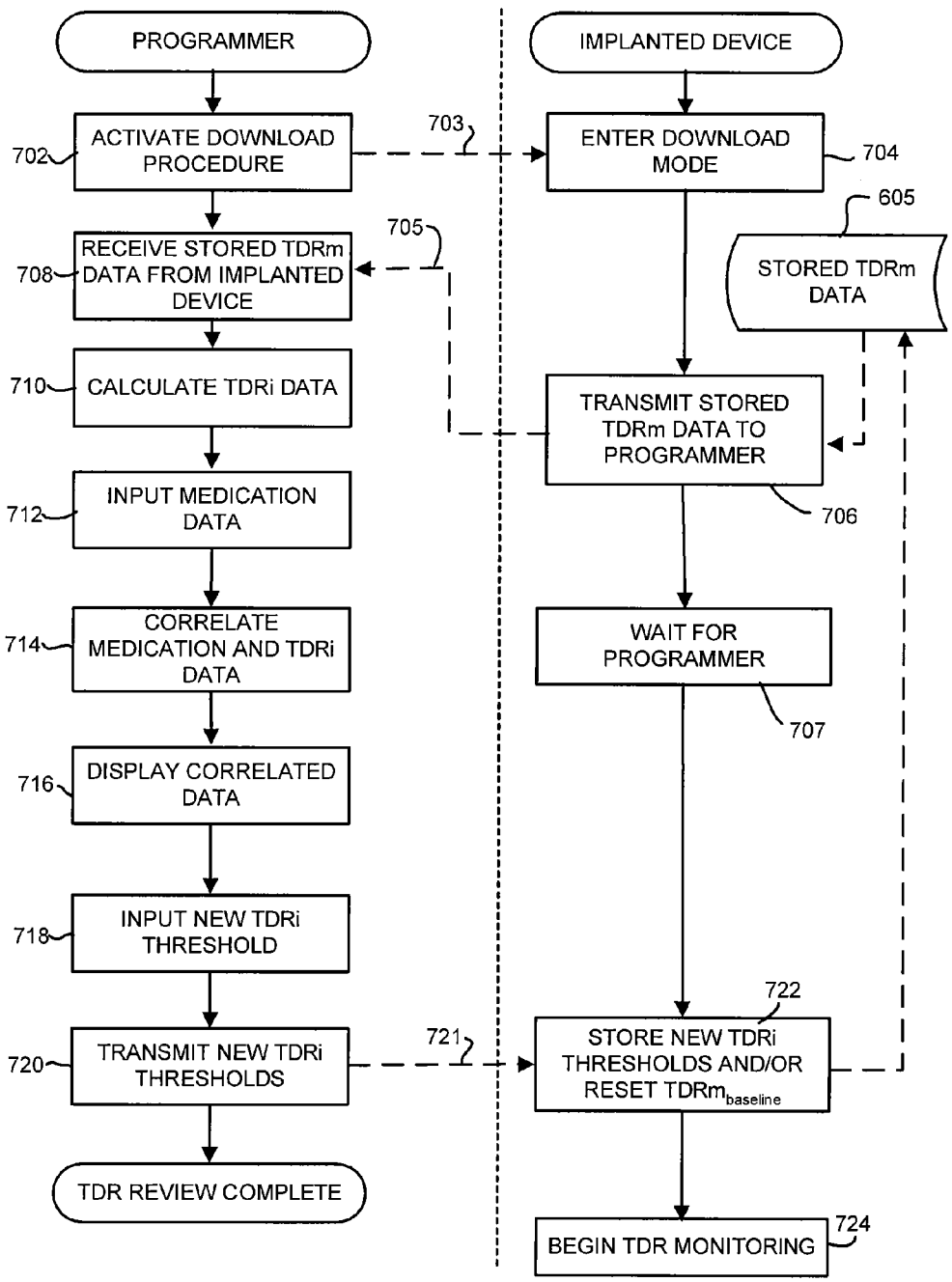
FIG. 7 is a flow diagram illustrating a method performed by the implantable cardiac stimulation device of FIG. 2 in combination with external data entry devices, such as shown in FIG. 4, to correlate changes in arrythmogenicity with changes in medication regimen and communicate such changes to the patient, physician, caregiver or manufacturer in accordance with one specific embodiment of the present invention.

In FIGS. 6 and 7, flow charts are provided illustrating the operation and features of certain embodiments of the invention. In the flow chart, various algorithmic steps are summarized in individual "blocks". Such blocks describe specific actions or decisions to be made or carried out as the algorithm proceeds. Where a microcontroller (or equivalent) is employed, the flow charts presented herein provide the basis for a "control program" that may be used by such a microcontroller (or equivalent) to effectuate the desired control of the device. Those skilled in the art may readily write such a control program based on the flow charts and other descriptions presented herein.

Referring now to FIG. 6, TDR monitoring is enabled at step 602. TDR monitoring may be enabled, for example, by a physician when prescribing a new medication to a patient. TDR monitoring may be enabled using a programmer 202 to access host controller 260 of cardiac stimulation device 110. TDR monitoring may be enabled by using an initiation signal (such as a magnet placed over cardiac stimulation device 110) to activate initiation circuit 232 of cardiac stimulation device 110.

At step 604, TDR monitoring unit 220 acquires EGM data for analysis of TDR. Data acquisition system 290 acquires cardiac electrogram signals, converts the raw analog data into digital signals, and stores the digital signals for later processing. Data acquisition system 290 is coupled to the right atrial lead 120, the coronary sinus lead 124, and the right ventricular lead 130 and the housing 240 through the switch bank 274 to sample cardiac signals across any pair of desired electrodes. TDR monitoring unit 220 may receive the EGM data as it is generated by data acquisition system 290 for analyzing TDR in real time. Alternatively, TDR monitoring unit 220 may read recorded EGM data from memory 294 when required for TDR analysis.

At step 606, TDR monitoring unit 220 identifies the relevant aspects of the T-wave of the EGM in the EGM data and calculates the value for a chosen metric of TDR ("TDRm") based on one or more morphological parameters of the EGM data acquired in step 604. This value is stored as a baseline value for TDRm ("TDRm$_{baseline}$") in stored TDRm data 605. As described above, any of the metrics of TDR known in the art may be used in accordance with the present invention. TDRm can be, for example, one of the following metrics of T-waves: $T_{amplitude}$, $T_{peak}$-$T_{end}$, $T_{slope}$, $T_{area}$, $T_{width}$, $T_{timing}$, $T_{morphology}$, QT interval, evoked QT interval, $T_{morphology}$, and $T_{complexity}$ (as measured by singular value decomposition). Furthermore, to enhance the calculation of the chosen metric, the T-wave properties may be measured over a predetermined number of beats (e.g., 2 to 20 beats). Alternatively, the value of TDRm can be calculated as a running average of its value over a certain time period (e.g., can be as long as 24 hrs). Alternatively, the current value of the TDRm can be calculated periodically (hourly/daily/bi-weekly), as an average representative of that period. At the end of step 606, the value of TDRm is stored in memory 294 as TDRm$_{baseline}$ in stored TDRm data 605.

At step 607, in this embodiment, TDR monitoring unit waits for a time "t" before again capturing or reading EGM data and calculating TDRm for a new time period. The length of the interval between measurements of TDRm in this embodiment is preferably selected by the physician and/or programmed into cardiac stimulation device 110 using programmer 202.

At step 608, TDR monitoring unit 220 acquires EGM data for the time period "t" after determination of baseline TDR. At step 610, TDR monitoring unit 220 identifies the relevant aspects of the T-wave of the EGM in the EGM data and calculates the value for the chosen metric of TDR ("TDRm") based on one or more morphological parameters of the EGM data acquired in step 608. The measured TDRm$_{baseline+t}$ may be stored in host controller 260 or memory 294 as part of stored TDRm data 605. The current value of TDRm is thereby calculated periodically (hourly/daily/bi-weekly), as an average representative of that period. In an alternative embodiment, the current value of TDRm can be calculated as a running average of its value over a certain time period. The time period can be for example one of 1, 6, 12 or 24 hours.

At step 612, TDR monitoring unit 220 generates TDRi by comparing TDRm$_{baseline+t}$ generated in step 610 with TDRm$_{baseline}$ generated in step 606. TDRi can be calculated, for example as percentage change in TDRm or rate of percentage change of TDRm as described above. At step 614, TDR monitoring unit 614 compares the TDRi generated at step 612 with acceptable bounds for TDRi. If TDRi is outside acceptable bounds, then at step 616 TDR monitoring unit 616 can cause host controller 260 to trigger a warning which may be communicated to the patient, a physician, clinician, nurse, caregiver etc. Where the medication administered is a medication intended to reduce the risk of arrhythmia the thresholds defining the acceptable bounds for TDRi may be configured to reflect that expected reduction in risk of arrhythmia. In this situation, a warning would be triggered in the event that the reduction in risk of arrhythmia was less than expected.

Depending upon the configuration of the implantable stimulation device 110, the warning signal may be generated by causing the pacemaker to periodically vibrate inside the patient. Alternatively, the pacemaker may transmit a warning signal to an external warning device such as a bedside monitor or a portable device 204 carried with the patient, which displays the warning for the patient. The warning may, for example, advise the patient to contact their cardiovascular physician. To facilitate such a warning, the bedside monitor or portable device 204 is preferably provided with an alarm 430 which is a device such as a vibrator, beeper or flashing light to draw attention of the patient to the portable device. Additionally, if the bedside monitor or portable device 204 is provided with a wireless modem 432, the warning signal may also be transmitted through communications server 409 and WAN 364, to other persons, such as the device manufacturer, a physician, nurse or caregiver as described with respect to FIG. 4. Additional details of external warning devices may be found in U.S. Pat. No. 7,142,911 (Boileau et al.) which is incorporated herein by reference.

In an alternative embodiment, if TDRi is outside acceptable bounds, TDR monitoring unit 220 may adjust the cardiac rhythm management parameters of cardiac stimulation device 110. For example, the new program parameters may be adjusted in preparation for the possibility of arrhythmia. In addition TDR monitoring unit 220 may send control signals to medication pump 203 to adjust the dosage of medication in response to the detected risk of arrhythmia.

TDR monitoring unit then returns to step 607 and waits for a second time period "t" before again capturing EGM data and calculating TDRm for the new data. The next TDRm measurement will be $TDRm_{baseline+2t}$. TDR monitoring unit can then compare $TDRm_{baseline+2t}$ to $TDRm_{baseline}$ to generate a new value for TDRi. In this way, the implantable stimulation device continues to monitor for changes in arrythmogenicity without user or physician intervention and can alert the physician, patient or other caregiver if changes in arrythmogenicity are outside acceptable bounds.

Correlating Changes in TDR with Changes in Medication

FIG. 7 is a flowchart illustrating one embodiment correlate changes in TDR with changes in medication. FIG. 7 illustrates steps performed by the programmer 202 of FIG. 3 and by the implantable stimulation device 110 of FIGS. 1 and 2 with steps performed by programmer 202 shown on the left and steps performed by implantable stimulation device 110 shown on the right. Programmer 202 is typically under the control of a medical professional such as cardiovascular physician charged with the care of the patient. The patient should make frequent visits to the physician to confirm that the cardiac stimulation device is programmed or operating correctly. The procedure of FIG. 7 may be performed at such regularly scheduled checkups. Also, the procedure of FIG. 7 may be carried out in response to a warning initiated by the TDR monitoring unit 220 to the patient, physician caregiver or manufacturer.

At step 702, programmer 202 activates the download of stored TDRm data 705 from cardiac stimulation device 110 by transmitting signal 703. At step 704, cardiac stimulation device receives signal 703 and enters download mode. At step 706, cardiac stimulation device transmits stored TDRm data 705 to programmer 202 and then enters wait state 707. At step 708, programmer 202 receives stored TDRm data 705 from cardiac stimulation device 110. In one example, the TDRm data 705 comprises a baseline TDRm ("$TDRm_{baseline}$") and a plurality of periodic subsequent TDRm values such as, for example, $TDRm_{baseline+t}$, $TDRm_{baseline+2t}$, $TDRm_{baseline+3t}$ ... $TDRm_{baseline+nt}$ (where n is the integral number of time periods t that have passed since initiation of TDR monitoring). The $TDRm_{baseline}$ is measured upon initiation of TDR monitoring by the cardiac stimulation device as described with respect to step 606 of FIG. 6. Preferably the time interval "t" between each subsequent time for which TDRm values is calculated was previously selected and programmed into cardiac stimulation device 110 by programmer 202. The TDRm data may also include TDRi values calculated by TDR monitoring unit 220.

At step 710, programmer 202 calculates TDRi based on the stored TDRm data 705. In one embodiment, programmer 202 plots TDRm against time and fits a line to the stored TDRm data using standard mathematical techniques. To standardize the data, $100\times(TDRm_{baseline+nt}-TDRm_{baseline})/TDRm_{baseline}$ may be plotted against time. Either the change in TDRm or the slope of the best fit line may be used as the TDRi for any time period chosen.

Where TDR monitoring was initiated prospectively to monitor the arrythmogenic effect of a medication, the arrythmogenic effects can be judged by the best fit straight line. In this embodiment, in step 712, the medication data is the identity of the medication taken and the time when the medication was commenced (and $TDRm_{baseline}$ was calculated). The slope of the best fit straight line is the average change in TDRm over baseline per unit time. At step 714, the data is correlated with the initiation of medication treatment and the data is analyzed to see if there was a long sustained change in TDRm following administration of the medication. The data may be displayed to the physician in graphical or other suitable formats at step 716 in order to aid the physician's analysis. In many case, if there is a long sustained increase in TDRm, this indicates that the medication is arrythmogenic for this particular patient and that the medication regimen should be modified. Alternatively, or additionally, the physician may decide to adjust the programming parameters of cardiac stimulation device 110 to compensate for the increase in risk of arrhythmia. Alternatively, where the medication administered is a medication intended to reduce the risk of arrhythmia, a long sustained change in TDRm indicating a reduction in risk of arrhythmia is the expected effect of the medication. In this situation, the lack of the expected changes in TDRm is an indication to the physician that the medication is ineffective at its present dose and that the dosage or the medication may need to be changed.

At step 718, the physician may input a new threshold for TDRi and/or reset $TDRm_{baseline}$ to the current value of TDRm for the patient. The physician may optionally adjust the time interval between calculations of TDRm and/or TDRi. The physician may also chose to continue or terminate TDR monitoring by cardiac stimulation device 110. At step 720 programmer 202 transmits the new TDR monitoring parameters 721 to Cardiac Stimulation Device 110. At step 722, cardiac stimulation device 110, ends its wait state, and receives and stores the new TDR monitoring parameters. If so selected by the physician, cardiac stimulation device 110 then commences TDR monitoring in accordance with the new parameters in step 724.

In an alternative embodiment, cardiac stimulation device maintains a rolling record of TDRm measurements and does not require an initiation signal from a physician in order to commence TDR monitoring. For this purpose, TDRm may be measured, for example, every 2, 6, 12 or 24 hours. Individual TDRm values or average TDRm values are stored each day. The TDRm records are maintained until the next visit to the physician and then downloaded to programmer 202. The TDRm data on implantable cardiac device 110 may then be erased. In this embodiment, the TDRm data may be retrospectively correlated with changes in medication regimen where an increase in arrhythmia is noted. The current TDRm data is downloaded from the cardiac stimulation device at step 708 and added to TDRm data (if any) previously downloaded from cardiac stimulation device 110. TDRi is then calculated for the TDRm data, TDRi may be calculated for periods of one to seven days depending on the granularity in changes of the patient's medication. The periods may also be selected based upon the timing of changes in the medication regimen of the patient. The data can then be correlated with the medication data in order to find any correlation between TDRi and the medication regimen. For example, at step 714, the TDRm data may be analyzed for a seven to 14 day period following the initiation of each change in medication regimen and the TDRm data analyzed to see if there was a long sustained change in TDRm following any change in medication regimen. In order to correlate changes in the medication data with the TDRm data, it is desirable that the medication information be as detailed as possible. Programmer 202 may receive such medication data from a variety of sources including the patient, pharmacists, other physicians or insurance companies. Programmer 202 may access such data from databases over WAN 364. The physician may also input such data based on information received from the patient. It is desirable that the medication data include both prescription and non-prescription medications. In many cases, if there is a long sustained increase in TDRm, this indicates that the medication is arrythmogenic for this particular patient and that the medication regimen should be modified. Alternatively, or in addition, the physician may decide to adjust the programming of cardiac stimulation device 110 to compensate for the increase in arrythmogenicity. It should be noted that the embodiment in which TDR monitoring is initiated in connection with a change in medication is a special case of this more general correlation method which uses a single medication data point i.e. the initiation of medication treatment at about the same time as the initiation of TDR monitoring.

Thus, programmer 202 may be used to correlate increases in risk of arrhythmia with changes in medication utilizing TDRi and TDRm data captured by implantable stimulation device 110. Programmer 202 may also be used to look for reductions in risk of arrhythmia expected following medication regimen changes intended to reduce the risk of arrhythmia. TDRm and TDRi are calculated in the same ways previously described, however, the expectation is that TDRm and TDRi will show a reduction in TDR over time following administration of the medication. Thus, where the medication administered is a medication intended to reduce the risk of arrhythmia, a long sustained change in TDRm indicating a reduction in risk of arrhythmia is the expected effect of the medication. In the event that programmer 202 does not detect the expected beneficial correlations, programmer 202 can provide a warning to the physician or other health care provider. Programmer 202 may also provide suggested modifications to the patient's medication regimen based in part upon the current medication regimen and the TDRm and TDRi data. Such modifications can be provided for example, by an expert system. Where the suggested modifications to the medication regimen are implemented, programmer 202 can examine later TDRi and TDRm data to determine whether the suggested modifications had the intended effect and suggest modifications again until an acceptable level of risk of arrhythmia is achieved. This essentially closed-loop system may allow for optimization of the medication regimen and minimization of the risk of arrhythmia for the particular subject.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. In an implantable system, a method for monitoring for an increase in arrhythmic vulnerability following administration of a medication other than an antiarrhythmic medication, comprising:
   (a) during a first time period, substantially coincident with commencing the administration of the medication other than an antiarrhythmic medication, obtaining an electrogram (EGM) signal from a patient via the implantable system, and analyzing one or more attributes of T-waves of the EGM signal to generate a first metric representative of transmural dispersion of repolarization (TDR);
   (b) during a second time period, following the administration of the medication other than an antiarrhythmic medication, obtaining a further EGM signal from the patient via the implantable system, and analyzing one or more attributes of T-waves of the further EGM signal to generate a further metric representative of TDR;
   (c) determining an index indicative of a total increase in arrhythmic vulnerability and an index indicative of a rate of increase in arrhythmic vulnerability following the administration of the medication other than an antiarrhythmic medication by comparing the further metric representative of TDR to the first metric representative of TDR; and
   (d) triggering an alert signal if at least one of the index indicative of the total increase in arrhythmic vulnerability or the index indicative of the rate of increase in arrhythmic vulnerability is outside of acceptable bounds defined by one or more thresholds;
   wherein steps (a), (b) and (c) are performed by the implantable system; and
   wherein the one or more attributes of T-waves analyzed at steps (a) and (b) is/are the same and comprise(s) at least one of an interval from an apex to an end of T-waves, a peak amplitude of T-waves, a slope of T-waves, an area under the curve of T-waves, a morphology of T-waves, or a complexity of T-waves.

2. The method of claim 1, wherein:
   step (a) includes storing, within a memory of the implantable system, the first metric representative of TDR generated for the first time period; and
   step (b) includes storing, within the memory of the implantable system, the further metric representative of TDR for the second time period.

3. The method of claim 2, wherein the first time period is triggered in response to a start signal received from outside of the patient.

4. The method of claim 3, wherein the start signal is received in association with administration of the medication other than an antiarrhythmic medication to the patient.

5. The method of claim 1, further comprising:
   (e) automatically adjusting delivery of the medication other than an antiarrhythmic medication by a medication pump in response to a change from the first metric representative of TDR to the further metric representative of TDR.

6. The method of claim 1, further comprising:
   (e) recording data regarding medication administered to the patient; and
   (f) comparing changes in arrhythmic vulnerability to the data regarding medication administered to the patient.

7. The method of claim 6, further comprising:
   (g) communicating the changes in arrhythmic vulnerability to an external system wherein the external system correlates said changes in arrhythmic vulnerability to the administration of the medication and suggests a change in the administration of the medication.

8. The method of claim 1, wherein the one or more attributes of T-waves comprises a complexity of the T-waves.

9. The method of claim 1, wherein the one or more attributes of T-waves comprises an interval from an apex to an end of the T-waves.

10. The method of claim 1, wherein the one or more attributes of T-waves comprises an area under the curve of T-waves.

11. A system for implantation in a patient, comprising:
a plurality of implantable electrodes configured to produce an electrogram (EGM) signal; and
a controller configured to:
  analyze one or more attributes of T-waves of an EGM signal obtained during a first time period, substantially coincident with administration of a medication other than an antiarrhythmic medication, to generate a first metric representative of transmural dispersion of repolarization (TDR);
  analyze one or more attributes of T-waves of an EGM signal obtained during a second time period, following the administration of the medication other than an antiarrhythmic medication, to generate a further metric representative of TDR;
  determine an index indicative of a total increase in arrhythmic vulnerability and an index indicative of a rate of change in arrhythmic vulnerability following administration of the medication other than an antiarrhythmic medication by comparing the further metric representative of TDR to the first metric representative of TDR; and
  trigger an alert signal if at least one of the index indicative of the total increase in arrhythmic vulnerability or the index indicative of the rate of increase in arrhythmic vulnerability is outside of acceptable bounds defined by one or more thresholds;
wherein the one or more attributes of T-waves obtained during the first and second time periods is/are the same and comprise(s) at least one of an interval from an apex to an end of T-waves, a peak amplitude of T-waves, a slope of T-waves, an area under the curve of T-waves, a morphology of T-waves, or a complexity of T-waves.

12. The system of claim 11, further comprising:
a memory configured to store the first metric of TDR generated for the first time period and the further metric of TDR generated for the second time period.

13. The system of claim 12, further comprising:
a receiver circuit configured to receive a start signal from outside the patient; wherein the first time period is triggered in response to the start signal.

14. The system of claim 11, further comprising:
a medication pump controller configured to adjust delivery of the medication other than an antiarrhythmic medication in response to changes in the metric representative of TDR.

15. The system of claim 11, wherein the one or more attributes of T-waves comprises a complexity of the T-waves.

16. The system of claim 11, wherein the one or more attributes of T-waves comprises an interval from an apex to an end of the T-waves.

17. The system of claim 11, wherein the one or more attributes of T-waves comprises an area under the curve of T-waves.

* * * * *